United States Patent [19]

Shaw

[11] 4,100,267

[45] Jul. 11, 1978

[54] METHOD OF DETECTING HEPATITIS B CORE ANTIGEN AND ANTIBODY

[75] Inventor: Eugene Douglas Shaw, Bridgewater, N.J.

[73] Assignee: Ortho Diagnostics Inc., Raritan, N.J.

[21] Appl. No.: 618,644

[22] Filed: Oct. 1, 1975

[51] Int. Cl.$^2$ ................. A61K 39/00; A61K 39/42; A61K 43/00; G01N 31/00

[52] U.S. Cl. ................................ 424/1; 23/230 B; 424/8; 424/12; 424/86; 424/89; 424/93

[58] Field of Search ................ 424/1, 8, 12, 86, 89, 424/93, 1.5; 23/230 R, 230 B

[56] References Cited

PUBLICATIONS

CDC, Morbidity & Mortality, HEW vol. 23, No. 4, Date of Release, Feb. 1, 1974, p. 29.
Shaw et al., Abstract of "Studies of A-2 Plaque Virus in Asso. with Viral Hepatitis", Program of ASCP, Fall Meeting Oct. 4-11, 1974, 1 page.
Almeida, Lab.-Lore, Welcome Service in Lab. Tech., Welcome Reagents, Burroughs Welcome Co., N. C., vol. 6, No. 6, Feb. 1975, pp. 337-340.
Shaw, J. of Virology, vol. 12, No. 6, Dec. 1973, pp. 1598-1607.
Shaw[2], IX Int. Cong. for Microbiology, Moscow, USSR, Abstract of Papers, 1966, p. 395.

*Primary Examiner*—Albert T. Meyers
*Assistant Examiner*—A. P. Fagelson

[57] ABSTRACT

The formation of antibodies to the A-2 plaque virus previously propagated in tissue culture is described. The application describes an immune response against those antibodies and against the A-2 plaque virus antigen which is associated with human viral hepatitis both of type A and B origin. The reaction of antibody for A-2 plaque virus with the antigen from stool specimens of volunteers infected with type A hepatitis and from the sera of patients diagnosed as having type B hepatitis is described. Convalescent sera from both type A and type B hepatitis patients in reaction with the virus, demonstrate the presence of antigenic components in the plaque virus which react with human antibody formed in response to infection with either type A or type B hepatitis. Moreover, the A-2 plaque antibodies react with hepatitis B core antigen, while antibodies to $HB_cAg$ react with A-2 plaque antigen. Additionally, methods for inducing antibody formation in humans from the A-2 plaque virus antigen are described, as are methods for detecting $HB_cAg$, $HB_cAb$, HAAg and HAAb.

6 Claims, No Drawings

METHOD OF DETECTING HEPATITIS B CORE ANTIGEN AND ANTIBODY

BACKGROUND OF THE INVENTION

This invention relates to the detection of antibodies and antigens and to vaccines and methods for immunizing against disease. More particularly, the invention relates to the production and propagation of a known virus and the use of that virus to induce antibody formation and the subsequent immunization of hosts especially humans against both type A and type B viral hepatitis. Specifically, it relates to the use of virus-derived materials in the prevention of type A and type B hepatitis, and to methods for detecting the presence of hepatitis B core antigen and antibody and hepatitis A antigen and antibody.

Hepatitis is a viral disease well known and frequently encountered in everyday life. The disease is intractable and is characterized by inflammation of the liver, jaundice, fever and other systemic manifestations. There are two types of hepatitis generally recognized, the so-called type A and type B, each of which is associated with a different virus.

The virus associated with type B viral hepatitis has been identified immunologically as Australia Antigen (HAA). Type A hepatitis is associated with a virus characterized simply as Hepatitis A Antigen. For purposes of shorthand notation and convenience of reference, Hepatitis A Antigen is frequently written as HAAg and Hepatitis B Antigen is commonly designated as HBAg.

The disease caused by each of these organisms is virtually clinically identical. While there may be some differences in incubation periods, the course of the disease generally follows the same clinical path. Initially, the infected patient may encounter headache, nausea, muscle cramps, fever, chill, fatigue and a general malaise. These symptoms can vary as to severity in individual patients, but are usually followed by what is known as the icteric phase of the disease wherein jaundice begins. The onset of the icteric phase usually comes somewhere between 29 and 100 days following infection depending on the species type of causative organism.

Antigen from Type B hepatitis (HBAg) in infected patients can usually be found in the serum, and often in the semen, saliva and urine of those patients. On the other hand, antigen from patients infected with A type hepatitis (HAAg) is found in the feces of those patients.

HBAg and HAAg are distinguishable under the electron microscope, especially by the technique known as immuno-electron microscopy (IEM). On that level, the A Antigen appears as particles roughly in the shape of icosohedrons, varying in size from approximately 25 to 30 nanometers (nm.). The hepatitis B virus is presently recognized as comprising a mixture of particles called Dane Particles and debris from the surface of the Dane Particle.

The Dane Particles are spheres which contain a coat protein covering a core particle generally the shape of an icosohedron. The Dane Particle spheres are generally observed in the 40 to 45 nm. size range, whereas the core of the Dane Particle appears in the range of approximately 27 to 30 nm. The debris from the Dane Particle spoken of above is usually comprised of disrupted parts of the coat or surface protein and is generally manifested in the form of spheres and tubules usually in the 20 to 25 nm. range. In hepatitis caused by hepatitis B virus, it is the core material of the Dane Particle which is the presumptive infective agent.

Still with reference to the Dane Particle, the coat surface protein thereof is designated as $HB_{surface}Ag$ (also $HB_sAg$) while the core material is designated $HB_{core}Ag$ (also $HB_cAg$). It is important to note that the Dane Particle surface protein ($HB_sAg$) and the debris represented in the B antigen are antigenically similar. That is, $HB_s$ antigen cross-reacts with antibodies produced from the debris of hepatitis B antigen. On the other hand, the Dane core particle ($HB_cAg$) is antigenically discrete from the Dane surface protein ($HB_sAg$). That is, $HB_cAg$ will not cross-react with antibodies induced by $HB_sAg$. Similarly, $HB_sAg$ will not cross-react with $HB_cAb$. (For purposes of shorthand notation, it is common in the art to designate the antibodies simply as, for example, $HB_sAb$). When the terms HBAg or HBAb are used in the literature, the designation usually means $HB_sAg$ or $HB_sAb$. That is, it is the surface antigen of the Dane Particle and/or the debris of the B antigen that is usually referred to. This is especially true of literature appearing before 1974, when the distinction between core antigen and surface antigen was not fully appreciated. Currently, the recommended nomenclature for antigens associated with viral hepatitis type B promulgated by the U.S. National Academy of Sciences - Committee of Viral Hepatitis of the National Research Council is as follows:

Cytoplasmic hepatitis B antigen (CHBAg) corresponds to hepatitis B surface antigen ($HB_sAg$), while nuclear hepatitis B antigen (NHBAg) corresponds to hepatitis B core antigen ($HB_cAg$). Antibody to CHBAg (CHBAb) corresponds to antibody to $HB_sAg$ (anti-$HB_s$), while antibody to NHBAg (NHBAb) corresponds to antibody to $HB_cAg$ (anti-$HB_c$).

As stated above, the presumptive causative organisms of viral hepatitis are two: $HB_cAg$ from hepatitis B virus and HAAg from hepatitis A virus. There is no core or surface distinction for hepatitis A Antigen, since the form of this particle is entirely different from that of the B virus. Immunologically, antibodies induced by B Antigen will not cross-react with A Antigen. Similarly, antibodies induced by A Antigen will not cross-react with B Antigen.

The importance of this will readily be understood by one skilled in the art. In order effectively to provide immunization against the onslaught of a viral attack, one would have to provide within a host an antigenic substance capable of inducing antibodies which would cross-react with the virus (i.e. the antigenic substance) involved in the attack. Therefore, in order to induce antibodies against hepatitis A virus, one would normally have to first induce in the host the formation of hepatitis A antibody. This would have to be accomplished by administering an antigenic substance capable of inducing those antibodies. The same may be said of the approach to preventing infection by hepatitis B virus. To date, no one has been able to produce a type A Antigen or type B Antigen outside of a host and for administration in an immunization procedure, and this has frustrated attempts at obtaining effective vaccine production.

PRIOR ART

The A-2 plaque virus was first isolated in 1963 at the Virology Branch of the Armed Forces Institute of Pathology (AFIP) by Dr. A. D. Felsenfeld. This virus was isolated from the sera of icteric-phase hepatitis patients with confirmed hepatitis B infection in a manner to be described below. In studies on the A-2 plaque virus, it was learned that the virus induced the production of antibodies which react with $HB_sAg$. This appeared in a publication dated December, 1973, appearing in the *Journal of Virology*, Volume 12, Number 6, pages 1598-1607 L by E. D. Shaw et al. The E. D. Shaw of that article is the same applicant herein. The contents of that article are incorporated herein by reference. This article is concerned with detection of the surface antigen of the hepatitis B virus and shows the preparation of the A-2 plaque virus, the propagation thereof in tissue culture and production of antisera to the virus in rabbits. It also shows the method of propagating the virus in serum-less media.

A specimen of the A-2 plaque virus used in the studies reported herein and in the above-mentioned article is on deposit at the American Type Culture Collection, Rockville, Maryland, and bears accession No. ATCC VR 812 and will be freely available to the public upon the issuance of this patent. The virus has not been taxonomically classified. Taxonomically, however, it has properties compatible with picornaviruses-enteroviruses. For example, the virus has a small diameter of the order of 27 to 29 nm.; has an RNA core; is heat resistant (that is, it survives 56° C. for one-half hour); resists divalent cations, for example, calcium and magnesium; resists bile salts, ether, actinomycin D and DNase; but is sensitive to RNase.

ISOLATION AND PROPAGATION OF A-2 PLAQUE VIRUS

In the previously-referred-to *Journal of Virology* December, 1973 article, there is indicated on page 1598 the method by which the A-2 agent was first detected in human icteric-phase sera. As pointed out therein, the sera began to exhibit cytopathic effect in human embryonic kidney (HEK) during its first passage. It was subcultured by three additional passages in Human Embryonic Kidney (HEK) followed by plaque purification under agar overlay in two passages in Porcine Kidney and then through various passages as desired in Primary African green monkey kidney (AGMK). Continued passages in AGMK do not alter the characteristics of the virus but are used simply to obtain large quantities for use. After selection and purification of the plaque-forming units (PFU) using agar overlay, the A-2 plaque virus was obtained.

As used herein, the term Plaque Forming Units (PFU) means that amount of virus obtained from tissue culture plaque formations described in Example I, for example, having a plaque diameter of approximately 2 mm. under agar overlay. An amount corresponding to $2 \times 10^6$ PFU per ml. of tissue fluid was equivalent to a $TCID_{50}$ (Tissue Culture Infective Dose) $10^{-5.7}$/0.1 ml. using standard tissue culture tube titrations. In the work described herein, A-2 plaque virus having gone through at least 45 passages through AGMK was used. Detailed propagation of A-2 plaque virus is described in Example I.

DESCRIPTION OF THE INVENTION

The present invention is based on the discovery that the A-2 plaque virus has the unique and remarkable ability to induce antibodies which cross-react with both hepatitis B core antigen and hepatitis A antigen. Similarly, the A-2 plaque virus antigen itself can cross-react with antibodies induced by hepatitis A antigen and hepatitis B antigen, both core and surface. Therefore, not only does this discovery now permit the production of a vaccine for hepatitis, but it additionally permits the production of a vaccine for humans which would immunize against both type A and type B viral hepatitis. This latter advantage, it will be appreciated by one skilled in the art, is remarkable, since in usual practice one encounters antigenic materials that are specific only to antibodies produced from that antigen.

As a further aspect of the invention, there is now provided a method for detecting the presence of type A or type B hepatitis antigens or antibodies in materials, especially body fluids or solids. This is of significant importance in the medical field.

With reference now to the production of vaccine and the method of utilizing the same in the immunization of humans, A-2 plaque virus is grown and propagated in tissue culture in accordance with known techniques. The live agent obtained from these techniques, as for example described in Examples I and II hereof, and the aforementioned Shaw et al. 1973 article, is used as the immunizing agent and can be directly administered to a host animal in an effective amount alone or admixed with a pharmaceutically acceptable medium as desired as the carrier. It is preferred to administer the virus parenterally in a pharmaceutically acceptable liquid and especially intramuscularly in a single dose injection. An effective amount of the material is one that comprises approximately $1 - 3 \times 10^8$ PFU of A-2 plaque virus in a volume of liquid conveniently handled such as one — three cc's.

As pharmaceutically acceptable media, there may be used the cell-free tissue culture growth material, Freund's adjuvant, isotonic saline, a serum-free medium such as that described by Leibovitz, *Amer. J. Hyg.* 78:173–180, and the like. It may be desirable under some circumstances to give a booster dose some several weeks after the initial administration in order to boost the level of antibody produced by the A-2 plaque virus. This can be accomplished using a similar dosage level of the material.

If desired, the live virus can be killed using known techniques and administered as a dead virus. Preferred would be the use of formalinized virus cells for administration systemically.

The method of the present invention involving use as a vaccine manifests itself as a method for inducing the formation in humans of antibodies of hepatitis B core antigen and hepatitis A antigen which comprises administering to a human an effective amount of purified A-2 plaque virus, preferably one corresponding to ATCC No. VR 812.

In yet another aspect of the invention, however, there is provided a method for detecting hepatitis B core antigen in a body material, preferably fluid or a fluid extract of such material, suspected of containing core antigen which comprises contacting said material in a system with antibodies to A-2 plaque virus, said virus preferably corresponding to ATCC No. VR 812, thereby to cause the core antigen if present to cross-react with the antibodies and produce thereby a detectable immunological reaction. The occurrence of that reaction indicates that the core antigen was present and the absence of that reaction indicates that the core antigen was not present. The difference between reaction and no reaction can be determined by selecting a minimum agglutination response below which negative values are ascribed and above which positive values are ascribed. Such a selection process is within the skill of the art.

One criterion for scoring the occurrence of the agglutination aggregation is that described by Feinstone et al. Science, 182:1026–1028 (1973) in which aggregates of 3 to 5 particles after reaction with sera are scored as positive. It is preferred, however, to regard a positive reaction as one in which there are at least two tight aggregates of preferably a three-dimensional grape-like cluster containing at least 14 particles in each antigen/antibody complex. This reaction, in clear positives, is often characterized by the presence of 200 or more viral particles. In addition, the viral particles within any aggregate should have a major number with hollow cores. The above is suitable when using IEM as the technique for observing the reaction. For CEP, however, simple observation of the precipitin band is quite suitable for detection of positives.

Similarly, the method of the invention can be applied to the hepatitis A antigen as well and in fact can be detected by using the antibody to the A-2 plaque virus as described above in connection with hepatitis B core antigen detection. Conversely, the invention provides a method for detecting antibody to both B core antigen and A antigen simply by using the A-2 plaque virus generated as described herein.

The specific immuno-detection system used to implement the method of the present invention is not critical, and may be any one of a number of art-known processes. It is preferred for very sensitive experimental research work to use immuno-electron microscopy (IEM). For commercial purposes, a radioimmunoassay technique or an immuno-counter-electrophoresis (CEP) method is suitable.

Similarly, particle agglutination tests using latex particles, red blood cells or the like may be employed as well. In such cases, it will be necessary to couple the A-2 plaque virus antigen or antibody to the particle for subsequent reaction with the suspected complementary partner. The technique for so doing, however, and methods for coupling are well-known and require no further discussion here.

The invention will be further explained by the following detailed examples which illustrate preferred embodiments thereof.

EXAMPLE I

Propagation of A-2 Plaque Virus in AGMK

Trypsinized suspensions of primary AGMK cells are propagated at 35° C. under partial $CO_2$ atmosphere into stationary confluent monolayers with types 5 and 40 simianvirus antibody in growth medium of 10% fetal calf serum in Eagle's Minimum Essential Medium (Earle's salts) containing penicillin and streptomycin. Within 5 to 7 days, the monolayers of tissue culture are ready for inoculation and propagation of A-2 plaque virus.

The tissue culture growth medium is decanted off the AGMK monolayers. A maintenance medium, either of serumfree L-15 medium (see Leibovitz, A. infra) or of Eagle's MEM with Earle's salts without serum but containing 50 micrograms Gentamicin per ml. is used in twice rinsing of the AGMK monolayers.

One ml. of seed A-2 plaque virus (ATCC No. VR 812 inoculum of approximately $2 \times 10^6$ PFU per ml. is sufficient to infect a 110 cm.² area of AGMK monolayers covered with 50 to 60 ml. of maintenance medium in a tightly sealed C-32 oz. tissue culture flask and is added thereto. After incubation at 36° C. for 24 to 36 hours in air-sealed flasks, the characteristic lytic cytopathogenic effect (CPE) for destruction of the AGMK monolayers is complete.

The flasks of infected tissue cultures, plus a negative tissue culture passage control flask, are frozen in situ at $-70°$ C. After alternate thawing and freezing of the infected tissue cultures has been done 2 or 3 times, the contents of the inoculated flasks are pooled. Clarification of cellular debris is made by centrifugation at 800 to 1,000 xg. for 20 to 30 minutes in the cold. The supernatant fluids of clarified A-2 plaque virus are dispensed into desired volumes for storage at $-70°$ C. This material can be used as seed for other subcultures. This material is on deposit with the ATCC accession No. VR 812 and contains approximately $2 \times 10^6$ Plaque Form Units per ml. equivalent to $TCID_{50}\ 10^{-5.7}/0.1$ ml. using standard tissue culture tube titrations.

EXAMPLE II

Concentration of A-2 Plaque Virus

The clarified A-2 plaque virus obtained in Example I was ultracentrifuged at approximately 100,000 xg. for 18 hours in the cold. A pelleted viral material was obtained and resuspended into the recovered supernatant fluid at concentrations ranging from $1 - 3 \times 10^8$ PFU/ml.

This material is useable as a live viral immunogen for use in immunizing hosts including humans. It may be inactivated as desired using normal techniques such as formalin deactivation. The live antigen may also be used in diagnostic techniques to detect antibodies as described below.

EXAMPLE III

Preparation of Antibodies for Anti-A-2 Plaque Virus

The A-2 plaque virus obtained in Example II (1 ml. containing $2 \times 10^8$ PFU) was injected sub-cutaneously on day 0 into each of 10 white New Zealand rabbits to stimulate antibody production. On days 3 and 5, a second and third injection respectively of 1 ml. each was given intravenously. Test bleeds were performed on days 12 through 14 to determine if the titers were sufficiently high. The rabbits showing sufficient titer was then exsanguinated on day 21. The serum was collected and pooled and the globulin fraction was precipitated with sodium sulfate using known techiques. The resulting fraction was then dissolved in phosphate bufferred saline and then dialized in the cold against the buffer for approximately 48 hours. The solution was collected and tested by counter-immunoelectrophoresis and found to have a titer of 1:64 against A-2 plaque virus and by immuno-electron microscopy (IEM) found to have a titer equal to or greater than 1:4,375 against the A-2 plaque virus obtained in Example II.

EXAMPLE IV

Detection of (1) $HB_cAg$ and (2) $HB_cAb$ (1) Hepatitis B core antigen is prepared from chimpanzee liver whose serum was positive for $HB_sAg$ using the technique of Barker, L. F., et al., Hepatitis B Core Antigen: Immunology and Electron Microscopy, J. Virology Vol. 14, No. 6, pp. 1552–1558 (1974). The core antigen was located in the radioimmunoassay $HB_sAg$ negative cesium chloride fraction as described in the Barker reference. The core antigen was confirmed as being HB$_c$Ag by independent IEM in reaction with a rhesus monkey hyperimmune hepatitis B core antibody reference reagent material supplied by the Reference Reagent Branch of the National Institutes of Allergy and Infectious Diseases (NIAID), a Branch of the National Institutes of Health, Bethesda, Maryland. Additionally, independent confirmation was obtained against chimpanzee serum known to contain complement fixation hepatitis B core antibody at a titer of 1:64.

A quantity of 0.2 ml. of the core antigen isolated according to the above procedure was mixed with 0.05 ml. of the rabbit anti-A-2 plaque virus obtained in Example III. Utilizing the IEM and CEP techniques, the reactions were evaluated for the formation of immune aggregates. These techniques indeed confirmed that aggregates formed indicating that the antibodies induced by the A-2 plaque virus cross-reacted with hepatitis B core antigen (HB$_c$Ag).

(2) a. The NIAID rhesus reference core antibody and the chimpanzee core antibody described above in part (1) were mixed in separate experiments with the A-2 plaque virus obtained in Example II and examined for cross-reactions. Immune aggregates were observed by IEM thus indicating that the A-2 plaque virus is an antigen which can detect the presence of hepatitis B core antibody.

(2) b. Serum specimens[1] from a human having clinical symptoms of hepatitis and diagnosed as having chimpanzee associated hepatitis were selected for evaluation. CEP tests using commercial HB$_s$Ab as the antibody confirmed that the patient was negative for HB$_s$Ag. The liver homogenate of Example IV(1), that is, the independently confirmed hepatitis B core antigen, was used in a direct and indirect-inhibition CEP test to confirm the presence or absence of core antibody. The test was positive for HB$_c$Ab. When the A-2 plaque virus antigen prepared in Example II was used as the antigenic material in the direct and indirect-inhibition CEP test, the presence of HB$_c$Ab was observed. This adequately demonstrates that the antigenic material represented by the A-2 plaque virus can detect the presence of HB core antibody.

[1]The specimens of sera from the above patient were collected at four different times, one at the onset of symptoms of the illness, the second about six weeks after the first, the third serum approximately three months after the first, and the fourth four months after the first. The first two sera were negative for HB$_c$Ab using the foregoing procedure. The third serum collected was positive as above indicated. A later specimen of serum was negative for core antibody.

Direct CEP testing is accomplished by commercial tests. See McKee, A. P. et al., (1973), Vox Sang. 24:80–83, for a description of low voltage CEP technique for detection of Australia Antigen, and the previously referred to December, 1973 article of Shaw et al. for indirect tests.

EXAMPLE V

Detection of (1) Hepatitis A Antibody and (2) Hepatitis A Antigen (1) Human volunteers who had been experimentally infected with type A viral hepatitis were selected. Both serum and stool specimens were collected from these patients before and after infection. Using techniques well known in the art, diagnosis of hepatitis A was confirmed by detecting type A particles in the stool. The presence of type A antibody in the convalescent serum was independently confirmed by cross-reacting the type A antigen obtained from the stool with the serum by IEM reaction.

In order to determine for purposes of the present invention that A-2 plaque virus antigen cross-reacts with type A antibody, specimens of the serum were collected from the above-mentioned volunteers (3 in number) and using the technique of CEP against the A-2 plaque virus antigen prepared in Example II, said convalescent and icteric sera were shown to be positive for HAAb previously confirmed as described above as the hepatitis A antibody. These tests on the specimens collected before infection were negative for HAAb as well as HAAg in the stool. The table below shows the results:

| | Serum | Direct CEP | Indirect CEP |
|---|---|---|---|
| 1. a) | Pre Inoc. | — | — |
| b) | Icteric | +(1:4) | — |
| 2 a) | Pre Inoc. | — | — |
| b) | Icteric | +(1:4) | +(1:4) |
| 3. a) | Convalescent | +(1:8) | +(1:8) |

2. Detection of Hepatitis A Antigen

Stool specimens from the volunteers mentioned above were collected. Two of the specimens had been coded positive and six were coded negatives. They were examined and tested by CEP reaction with the rabbit globulin antibody for the A-2 plaque virus produced in Example III. Direct reactions were observed in the two coded positives but not in the six coded negative stool specimens.

In this example, fibrin was precipitated from the plasma with a ratio of 1 volume of 1 M $CaCl_2$ to 40 fluid from centrifugation at 2,000 × 9 for 15 minutes in the cold.

Stool suspensions were diluted in normal saline from the initial 1:5 to a final concentration of 1:25 prior to clarification of debris by centrifugation at 1,000 × *g* for 10 minutes. After further dilution in normal saline, each stool suspension was pelleted at 93,000 × *g* for 3 hours in the cold and resuspended in minimal amounts of normal saline. Thus, the fecal antigens could be diluted to required quantities for reaction at 37° C. for 30 minutes with either the selected pre-inoculation or convalescent sera. The fecal antigen-antibody reaction mixtures were diluted 1:2 in sterile-filtered distilled water.

EXAMPLE VI

Detection of Type A Hepatitis Antibody

Three white-lipped marmosets were infected with type A hepatitis. The marmoset at the time the study reported jerein was done, was the only animal aside from humans known to be susceptible to hepatitis A infection.

Coded pre-inoculation sera and coded convalescent sera were each evaluated by counter-immunoelectrophoresis (CEP) for A-type antibody using A-2 plaque virus from Example III with the following results:

| | Sera | Direct | Indirect | IEM |
|---|---|---|---|---|
| Animal 1 | Pre Inoc. | — | — | — |
| | b) Conv. Serum | + | — | + |
| Animal 2 | a) Pre Inoc. | — | — | — |
| | b) Conv. Serum | + | — | + |
| Animal 3 | a) Pre Inoc. | — | — | — |
| | b) Conv. Serum | — | — | — |
| Animal 4 | Normal Marmoset | | | |

| Sera | Direct | Indirect | IEM |
|---|---|---|---|
| Control | | | |

As can be seen, direct CEP correctly identified all the negative and all but one positive sera (3b) while indirect CEP failed to detect inhibiting A-2 plaque antibody. IEM gave the same reaction as 3b but later was judged positive by re-examination using the preferred criteria of judging IEM reaction aggregates reported hereinabove.

EXAMPLE VII

Two chimpanzees were each given one injection of 1 ml. of a 1:5 dilution of unheated $HB_s$ antigen (titer of 1:180 by Commercial CEP - Hapindex Ortho Diagnostics Inc., Raritan, New Jersey). Preinoculation sera were negative for $HB_s$ antigen as well as $HB_s$ antibody and antibody for the A-2 plaque virus.

Serum collected from the first chimp (No. 81) on the 21st day following inoculation, reacted against A-2 plaque virus showing that he had produced $HB_cAb$ cross-reactive with A-2 plaque antigen. Convalescent sera 5 1/2 months after injection became positive for $HB_s$ antibody as well as antibody for A-2 plaque virus by direct and indirect-inhibition CEP and IEM for A-2 plaque virus. Chimp No. 83 followed the same pattern of serology except that seroconversion occurred later. In both cases, the animals were negative for clinical symptoms of hepatitis and never became $HB_s$ antigen positive.

What is claimed is:

1. The method for detecting hepatitis B core antigen in a material suspected of containing said antigen which comprises contacting said material in a system with antibodies to A-2 plaque virus thereby to cause said antigen if present to cross-react with said antibodies, and then determining whether said cross-reaction has occurred.

2. The method according to claim 1 wherein the antibodies are antibodies to A-2 plaque virus corresponding to ATCC No. VR 812.

3. The method of claim 2 wherein sad system is an immuno-counterelectrophoresis, radioimmunoassay or immunoelectron microscopic system.

4. The method for detecting hepatitis B core antibody in a material suspected of containing said antibody which comprises contacting said material in a system with A-2 plaque virus antigen thereby to cause said antibody if present to cross-react with said antigen, and then determining whether said reaction has occurred.

5. The method according to claim 4 wherein the A-2 plaque virus antigen corresponds to ATCC No. VR 812.

6. The method of claim 5 wherein said system is an immuno-counterelectrophoretic, radioimmunoassay or immunoelectron microscopic system.

* * * * *